United States Patent [19]

Tsurumizu et al.

[11] Patent Number: 5,135,739
[45] Date of Patent: Aug. 4, 1992

[54] NON-CARIOGENIC COMPOSITION AND DRINK

[75] Inventors: Takashi Tsurumizu, Ichikawa; Takashi Hashimoto, Chofu; Makoto Sato, Tokushima, all of Japan

[73] Assignee: Kitasato Kenkyusho, Tokyo, Japan

[21] Appl. No.: 798,870

[22] Filed: Nov. 25, 1991

Related U.S. Application Data

[63] Continuation of Ser. No. 680,024, Mar. 28, 1991, abandoned, which is a continuation of Ser. No. 554,062, Jul. 16, 1990, abandoned, which is a continuation of Ser. No. 405,040, Sep. 8, 1989, abandoned, which is a continuation of Ser. No. 265,292, Oct. 26, 1988, abandoned, which is a continuation of Ser. No. 022,559, Mar. 9, 1987, abandoned, which is a continuation of Ser. No. 754,564, Jul. 12, 1985, abandoned, which is a continuation-in-part of Ser. No. 530,144, Sep. 7, 1983, abandoned.

[30] Foreign Application Priority Data

Feb. 15, 1983 [JP] Japan .................................. 58-23200

[51] Int. Cl.$^5$ .................. A61K 7/28; A61K 39/02; A01N 63/00
[52] U.S. Cl. .................................... 424/50; 424/92; 424/93 H
[58] Field of Search ............................ 424/50, 92, 93

[56] References Cited

U.S. PATENT DOCUMENTS

| | | | |
|---|---|---|---|
| 1,851,165 | 3/1932 | Farr | 424/93 |
| 1,899,817 | 2/1933 | Matt | 424/93 |
| 2,944,941 | 7/1960 | Goldenberg | 424/50 |
| 4,133,875 | 1/1979 | Hillman . | |
| 4,147,773 | 4/1979 | Ogasa | 424/93 |
| 4,314,995 | 2/1982 | Hata et al. | 424/93 |
| 4,337,314 | 6/1982 | Oeschger et al. | 424/92 |
| 4,345,032 | 8/1982 | Hata | 424/93 |
| 4,396,631 | 8/1983 | Adachi et al. | 424/93 |
| 4,442,085 | 4/1984 | Colman et al. | 424/92 |

FOREIGN PATENT DOCUMENTS 1375866 11/1974 United Kingdom .

OTHER PUBLICATIONS

The Journal of Dental Health, vol. 28 No. 2, JPA 47970/82, including English translation.

Primary Examiner—Nathan M. Nutter
Attorney, Agent, or Firm—Schweitzer Cornman & Gross

[57] ABSTRACT

Non-cariogenic composition, which comprises as active ingredient the living cells of a Human type strain of Streptococcus mutans capable of inhibiting the growth of cariogenic strains of S. mutans and incapable of inducing dental caries, in association with a carrier or excipient suitable for oral administration, said strains of S. mutans being isolated from the oral cavity of humans as naturally-ocuring strains. The non-cariogenic composition may be administered orally in the form of liquid, semi-solid or solid compositions, preferably in the form of yougurts containing edible lactic acid-producing bacilli or in the form of a freeze-dried composition containing such edible lactic acid-producing bacilli. The non-cariogenic composition may prevent or at least inhibit human dental caries induced by cariogenic S. mutans and moreover effective against other cariogenic oral bacilli such as edible lactic acid-producing bacilli known per se. Direct administration to human oral cavity may be effected simply and safely since the used effector strains are naturally-occurring strains in the oral cavity of humans.

11 Claims, No Drawings

NON-CARIOGENIC COMPOSITION AND DRINK

This application is a continuation of application Ser. No. 680,024, filed Mar. 28, 1991, which is a continuation of application Ser. No. 554,062, filed Jul. 16, 1990, which is a continuation of Ser. No. 405,040, filed Sep. 8, 1989, which is a continuation of Ser. No. 265,292, filed Oct. 26, 1988, which is a continuation of Ser. No. 022,559, filed Mar. 9, 1987, which is a continuation of Ser. No. 754,564, filed Jul. 12, 1985, which is a continuation-in-part of Ser. No. 530,144, filed Sep. 7, 1983, all now abandoned.

BACKGROUND OF THE INVENTION:

1. Field of the Invention

This invention relates to a non-cariogenic composition and drink for preventing or at least inhibiting human dental caries induced by *Streptococcus mutans* and other cariogenic bacilli.

2. Description of the Prior Art

Dental caries is a disease of teeth of humans and animals, which is induced by the action of cariogenic oral bacilli. Among them, *Streptococcus mutans* is believed to be most important. It has, hitherto, been disclosed, for example, in Bergy's Manual of Determinative Bacteriology, page 504 (1974) that a relationship exists between dental caries and *Streptococcus mutans*, it being suggested that *S. mutans* is a similar microorganism to *S. salivarius*, even though *S. mutans* has not yet been extensively studied and compared with *S. salivarius*. Nowadays, however, *S. mutans* which produces dextran-like polysaccharides (hereinafter referred to as DPS) from sucrose, is clearly distinguished from *S. salivarius* which produces fructans from sucrose. Strains of *S. mutans* adher to the surface of the teeth of humans and animals and form dental plaque which is solid and adhesive. The major portion of *S. mutans* in the oral cavity resides in the plaque and produces lactic acid which directly breaks down the teeth. Even though other oral bacilli also produce lactic acid, the lactic acid produced by *S. mutans* is not released but is accumulated on the surface of the teeth. Thus, for example, British Patent 1,375,866 discloses that the formation of pre-carious dental plaque is a prerequisite for the development of dental caries and that glucosyltransferease is an important factor in the development of dental caries. It is said that the main constituents of insoluble and water-soluble DPS produced by *S. mutans* are high molecular weight polymers of glucose comprising respectively $\alpha(1-3)$ and $\beta(1-6)$ bondings (Guggenheim, Internat. Dent. J., 20:675-678, 1980).

There are known various other cariogenic microorganisms other than *S. mutans*. For example, it is well known that certain bacilli conventionally used for the preparation of yogurt, cheese and various other foodstuffs containing lactic acid-producing bacilli have cariogenic potential. For example British Patent 1,375,866 discloses that *Lactobacillus acidophilus*, *L. casei* and *Streptococcus faecalis* are well known aetiological factors. Oshima also reported that *L. casei* and *L. helvetius* used for yogurts commercially available in Japan induced dental caries (The Japanese Journal of Pedodontics, 16, 1. 161-169, 1978 in Japanese version). Even though the cariogenic potential of other cariogenic bacilli is not higher than that of *S. mutans*, for example, they intrude into dental caries already induced by *S. mutans* and reside there. In such a case, for example, lactic acid and acetic acid produced by them do harm to the structure of the teeth.

It is known to inhibit (as hereinbefore defined) dental caries induced by *S. mutans* by using dental vaccine. Thus, for example, said British Patent 1,375,866 discloses a dental vaccine comprising as antigen the whole cells of *S. mutans* Strain SSC having the same characteristics as the characteristics of *S. mutans* NTCT 10449 which is a well-recognized cariogenic wild type strain of *S. mutans*. However, it is said that the usu of the whole cells (especially, the living whole cells) of cariogenic strains of *S. mutans* as antigen, can give rise to various undesired side effects such as allergic reaction and cross reaction with the heart muscle antigen, when administered to animals.

The use of bovine milk containing anti-S. mutans antibodies for inhibiting dental caries induced by *S. mutans* is also known (British Patent 1,505,513). However, the known bovine milk antibodies may not be used in practice since the resultant antibodies cannot inhibit *S. mutans* NCTC 10449, a well-recognized cariogenic strain of Human type *S. mutans*.

Apart from the known immunological methods, U.S. Pat. No. 4,133,875 to Hillman (1979) discloses to control human dental caries induced by cariogenic strains of *S. mutans* by the use of non-virulent analogs of cariogenic *S. mutans*. Such a method is based upon the socalled bacterial interference which appears, in general, to involve a competitive and/or antibiotic reaction of the non-virulent strains viz. the effector strain on its pathogenic counterpart and that such a strain must be (a) non-virulent as itself and (b) able to successfully compete with its pathogenic counterpart (cf. U.S. Pat. No. 4,133,875, column 3, lines 5-15).

Hillman discloses two effector strains, *Streptococcus mutans* JH140 (ATCC 31341) and JH145 (ATCC 31377), both isolated from streptomycin-resistant *S. mutans* BHT-2 (str.), followed by mutagensis. The biological characteristics of two effectors strains are, for example, as follows:

(a) inability to produce a detectable amount of lactic acid when incubated in the presence of glucose;

(b) relatively better adhesion to hydroxypate than the parent strain; and (c) higher productivity of plaque than the parent strain when incubated in the presence of sucrose.

However, *S. mutans* JH140 and JH145 did not give good result when used in practice for controlling human dental caries and, by way of example, the following problems arose:

(1) *S. mutans* is highly mutative and is classified into certain strain types. For example, Bratthall classified *S. mutans* into 5 serotypes (a to e) in view of the immunological specificities of the polysaccharides contained in the cell wall (Odont. Revy., 20:143, 1970; ibid. 20:13-27, 1970; and Perch et al, Microbiol. Scand Section B. 82:357, 1974).

Makoto Sato, one of the coinventors of this invention, has classified *S. mutans* into Human I (HI), Human II (HII) and Rat (R) types with respect to the specific antigens of *S. mutans*, which respectively correspond to said "'c', 'e' and 'f'", "'d' and 'g'" and "'a' and 'b'" serotypes. Sato has reported:

(a) 93.9% of *S. mutans* of human origin were Human I type and the rest was Human II type;

(b) all strains of rat origin were Rat type;

(c) no *S. mutans* was isolated from mice and guinea pigs; and (d) all strains originating from hamsters and monkeys were Human I type. (Journal of Dental Health. Vol. 28, No. 2, pages 99–123, 1978 in Japanese version).

However, BHT-2, the parent strain of JH140 and JH145 are the well known strain of Rat type *S. mutans* which has bever been isolated from humans and which differs from Human type strains. What will happen by administering Rat type strain to humans is not yet entirely clear.

(2) JH140 and JH145 form a large amount of plaque and have a higher ability to adher than the parent strain. However, it is common knowledge in the art that the formation of plaque and adhesion to the surface of the teeth result in the induction of dental caries.

3. Objects of the Invention

As is well known, *S. mutans* is highly mutative and has been classified into certain types. However, the competitive relationship between different strain types has not yet been completely clarified. In order to solve this question, we have produced many mutant strains by treating various wild type strains of *S. mutans* with mutagents such as, for example, nitrogen mustard, nitrosoguanidine or iradiation of ultraviolet rays etc. and have studied their characteristics such as, for example, colonial characteristics, biological characteristics, cariogenic potentials and the like. As a result, we have classified the mutational phases of *S. mutans* into the following 3 phases in disregard of their strain types:

(1) Phase I

"Normal" phase viz. the mutational phase of cariogenic wild type strains present in the oral cavity of humans and animals. When cultured on a sucrose-containing agar plate medium such as, for example, TYC agar plate medium (Stoppelaar et al, Archs. Oral Biol., 12, 1199–1201, 1967), solid colonies covered with a large amount of insoluble DPS are formed. Each colony has an irregular and raised margin and its central area is rough. There are minor morphological difference between respective colonies. The plaque formed is abundant, solid and adhesive and adhers to the tube wall and on the surface of the teeth. The productivity of lactic acid is high, and the cariogenic potential is highest of all 3 phases.

(2) Phase II

Essentially unstable phase, obtainable by treating Phase I viz. wild type cariogenic strain by mutagent. Also this phase occur sometimes by subculturing Phase I. There is a mutational variability between Phases I and II. When cultured on a sucrose-containing agar plate medium, round colonies like water-drops are formed, which are bright and somewhat mucoid. There are considerable morphological difference between respective colonies. The productivity of lactic acid and cariogenicity are weaker than those of Phase I.

(3) Phase III

Obtainable by treating Phase I with mutagent. Various characteristics of this phase are entirely different from the characteristics of other phases. For example, when cultured on a sucrose-containing agar plate medium, the colonies formed are round, bright, opaque smooth and large. In the test tube, the productivity of lactic acid is low, and other acids than lactic acid are substantially reduced. The ability to produce insoluble and water-soluble DPS is substantially reduced.

With respect to the competitive relationship between Phases I and III, it has been found that Phase III strains are capable of inhibiting the growth of Phase I strains in coexistence with them in vitro and in vivo. Where Phase III is introduced into a culture or into the oral cavity of animals where the plaque has been formed by the action of Phase I strains, Phase III intrudes into the plaque to "reside" there so that Phase I strains are outwardly destroyed and gradually disappeare owing to the loss of residence. Phase III strains also die owing to the loss of their support medium and inability to form new plaque. Where Phase I is introduced into a test tube or oral cavity already occupied by Phase III strains, Phase I strains die.

Various characteristics of Phase III are genetically stable. For example, no reversion to the parent strains was observed nor was there any observable generation of other mutant strain by subculturing on various media such as, for example, TYC agar plate media and no such effects were observed when continuously administered to hamsters, both subculturing and continuous administration being effected over an extended period of time (more than 6–12 months).

Based upon the above-mentioned discovery, Tsurumizu and Hashimoto, the coinventors of this invention, proposed a dental vaccine, comprising as active ingredient the living cells of *Streptococcus mutans* Attenuated Strain K-III (FERM BP 316) which they produced by treating a cariogenic strain of *S. mutans* isolated from the oral cavity of a human with mutagent (disclosed in Japanese Patent Application 47970/82 filed on Mar. 25, 1982 and laid open to public inspection on Sep. 29, 1983). Said K-III strain exhibits good results when used for inhibiting human dental caries induced by *S. mutans*. However, with respect to the commercial value of Phase III mutant strains, for example, the following problems arose: (a) very complicated procedure is required for obtaining official license for the commercial production of vaccines, and moreover (b) in many countries of the world, it is, as a rule, extremely difficult or impossible to use the viable cells of mutant strains obtained by treating virullent microorganisms with mutagents, for example, as additive to foodstuffs.

In order to overcome such difficulties and also eliminate the need for further processing which would otherwise be necessary to enable direct and safe administration into the oral cavity of humans, we have collected very many strains from the oral floras of more than 1000 humans and have compared their characteristics with the charcteristics of Phase III strains which we have induced from various cariogenic strains of *S. mutans*. As a result, it has unexpectedly been found that strains of *S. mutans* having analogous characteristics to the characteristics of Phase III mutant strains (hereinafter referred to as Phase III-like strains) are living in the oral cavity of minor humans, particularly, children and infants. It should be noted in this reagrd that no or little, if any, dental caries is observed in the oral cavity of the human hosts of Phase III-like strains. The reason why such unique strains exist preferably in the oral floras of children and infants is not yet clear. We have succeeded to isolate and purely culture various Phase III-like strains. It has been confirmed that Phase III-like strains are capable of effectively competing with cariogenic strains of *S. mutans* and moreover capable of inhibiting various other cariogenic oral bacilli in the oral cavity of humans with good result.

An object of the present invention is to provide a non-cariogenic composition for inhibiting (as hereinbefore defined) human dental caries, which may be used simply and safely with good results.

SUMMARY OF THE INVENTION

According to the present invention, there is provided a non-cariogenic composition for preventing or at least inhibiting human dental caries, which comprises as active ingredient the viable cells of at least one mutant strain of Streptococcus mutans which is capable of inhibiting the growth of cariogenic strains of Streptococcus mutans and incapable of inducing dental caries and which is isolated as a naturally-occuring strain from the oral cavity of humans, in assiciation with a carrier or excipient suitable for oral administration.

The following characteristics of Phase III-like strains are similar to the characteristics of Phase III strains and also similar to the characteristics of S. mutans NCTC 10449 otherwise specified.

I. Morphology

Streptococcus mutans, 1×1-2 microns, Gram-positive.

II. Growth on various media (37 C, 24 h., specified pH):

(1) TYC agar plate medium (Stoppelaar et al, Oral Biol., 12, 1199–1201, 1976):

Insoluble and water-soluble DPS are not produced. Colonies are round, flat, white, opaque, bright and large.

(2) Todd Hewitt Broth agar plate medium (Baltimore Bilogical Laboratories, Inc., U.S.A., hereinafter referred to as BBL):

Colonies are round, flat, opaque, bright, somewhat mucoid and large.

(3) Mitis-salivarius agar plate medium (Difco., U.S.A.):

DPS are not produced. Colonies are round, pale whitish, somewhat mucoid and large.

(4) Brain Heart Infusion agar plate medium (BBL):

Colonies are round, somewhat whitish, opaque and large.

(5) Tryptocase Soy Broth (BBL):

Growing from the lower layer of the medium.

(6) Todd Hewitt Broth (BBL):

Growing from the lower layer of the medium.

III. Physiological characteristics (1) Productivity of wire plaque (showing the adhering abity by insoluble DPS): negative.

(2) Agglutination of cells by DPS: negative, determined by the Freedman et al method with reference to Infect. Immun., 10, 189–196, 1974 and using Dextran T250 (Pharmacia Fine Chemicals AB., Sweden).

(3) Formation of pigment: negative.

(4) Growth range: pH 5–8, temperature 10°–39° C.

(5) Decomposition of sugars: Cf. Tables 4 and 1.

IV. Miscelleneous

Hydrolysis of esculin . . . positive; hemolysis (sheep) . . . from positive to negtive; glucosyltrnasferase activity . . . substantially deficient; productivity of lactic acid* . . negative (* Phase III . . .low); ability to infect to animals . . . negative.

V. Cariogenictiy: substantially deficient

VI. Serotype: Human I or II type

VII. Stability

Where, for example, the strain was subcultured over an extended period of time (more than 6 months) on TYC agar plate medium (pH about 7.3; 37° C.; 24 hours) or treated with known mutangents such as, for example, nitrogen mustard, nitrosoguanidine, irradiation of ultraviolet rays and the like, no reversion to the parent strain nor any generation of cariogenic mutant strain was noted. Generation of new dental caries, increase in the antibody titre in blood and serum and various other undesired side effects were not found to any asignificant degree on administering the living cells to humans and animals over an extended period of time.

VIII. Interference between Phase III-like strains and other cariogenic strains

In vitro and in vivo, Phase III-like strains are active as excellent effector strains against cariogenic strains of S. mutans of other phases, and moreover inhibit the growth of other cariogenic oral bacilli than S. mutans, probably because Phase III-like strains are incapable of forming plaque or residence so that they compulsively intrude into the support media of other oral bacilli and they are destroyed outwardly. The follollowing tables indicate that the characteristics of Phase III mutant strains and Phase III-like naturally-occuring strains are quite similar to each other. In these tables, the enzymatic activities, protein N and agglutination titres were respectively determined by the Inoue et al method (J.of Dental Health, 24, 6–18, 1974 in Japanese version), the E. P. Hartree method (Anal. Biochem., 48, 422, 1972) and the Sato method (one of the coinventors of the present invention, J. Dental Health, 28, 2, 99, 1978).

The following Table 1 shows the decomposition of sugars by Phase III mutant strains produced in a similar manner to that described in the reference hereinafter by the use of the following well-recognized cariogenic strains of S. mutans:

HS-1 (a), PA-1 (b), Ingbritt (c), NCTC 10449= ATCC 25175 (c), OMZ176 (d), P-4 (e), OMZ175(f), K1R (g) and RC-20 (b) (the serotypes are indicated in the brancket).

Other descompositions are the same as the decompositions by NCTC 10449, a typical cariogenic strain of S. mutans. In Table 1, the corresponding figures by Streptococcus mutans Attenuated Strain K-III (a Phase III strain produced by the method hereinafter described in Reference) are also shown.

TABLE 1

| Decomposition of sugars (Phase III mutant strains) | | | |
|---|---|---|---|
| Sugars | Phase 1 | Phase II | Phase III |
| Raffinose | # (1) | — | + |
| Salicin | — | # (4) | + |
| Cellobiose | # (2) | — | + |
| Mellibiose | # (3) | — | + |
| Esculin* | + | + | # (5) |

Notes:-
*Generaly weak and may vary with differing the individual strains.
...negative or positive.
(1) +....Ingbritt; (2) +....NCTC10449, OMZ176 and RC-20; (3) +....Ingbritt; (4) +....HS-1, P-4 and RC-20.; (5) —....S. mutans Attenuated Strain K-III (FERM BP 316)

The following Table 2 shows (A) sucrose activity (X10 U/mg of protein N), (B) glucosyltransferase activity (X10 U/mg of protein N), (C) invertase activity (X10 U/mg of protein N) and (D) Phase III strains induced from the cariogenic strains of S. mutans by the method of the hereinafter described reference. The reduction rates (parent strain=100%) of the enzymatic activities and protein N are also indicated. In Table 2, * and ** indicates respectively Human I and II type strains, and K-III indicates S. mutans Attenuated Strain K-III (FERM BP-316; NRRL B-15429).

TABLE 2

| (enzymatic activities and protein N of Phase III) | | | | | |
|---|---|---|---|---|---|
| Strain | Phase | A | B | C | D |
| HS-1(a) | I | 469. | 148. | 321. | 0.027 |

TABLE 2-continued (enzymatic activities and protein N of Phase III)

| Strain | Phase | A | B | C | D |
|---|---|---|---|---|---|
| | III | 25.3 | 11.2 | 14.1 | 0.031 |
| | % | 5.39 | 7.57 | 4.39 | 114.8 |
| FA-1(b) | I | 476. | 394. | 82. | 0.021 |
| | III | 17.4 | 7.6 | 9.8 | 0.029 |
| | % | 3.66 | 1.93 | 11.95 | 138.1 |
| Ingbritt(c)* | I | 484. | 235. | 239. | 0.0127 |
| | III | 49.4 | 41.4 | 8.0 | 0.017 |
| | % | 10.21 | 17.62 | 3.35 | 133.9 |
| 10449(c)* | I | 915.8 | 380.1 | 535.7 | 0.013 |
| | III | 23.7 | 13.3 | 10.4 | 0.026 |
| | % | 2.59 | 3.50 | 1.94 | 200.0 |
| P-4(c)* | I | 449. | 148. | 311. | 0.016 |
| | III | 57.6 | 38.7 | 19.0 | 0.021 |
| | % | 12.83 | 26.15 | 6.11 | 131.3 |
| OMZ175(f)* | I | 432. | 188. | 245. | 0.024 |
| | III | 46.7 | 21.2 | 25.4 | 0.033 |
| | % | 10.4 | 11.28 | 10.4 | 137.5 |
| K1R(g)** | I | 373. | 232. | 152. | 0.028 |
| | III | 43.4 | 16.7 | 27.8 | 0.031 |
| | % | 11.64 | 7.20 | 18.29 | 110.7 |
| RC-20(b) | I | 544.3 | 259.2 | 285.1 | 0.022 |
| | III | 16.8 | 4.2 | 12.5 | 0.031 |
| | % | 3.09 | 1.62 | 4.38 | 145.5 |
| K-III(c)* | III | 27.0 | 9.0 | 18.0 | 0.020 |

*..Human I type; **Human II type; ( )..serotype;
A..sucrase, B..glucosyltransferase and C..invertase (× 10 U/mg of protein N);
D..protein N (mg/ml)
Strain...parent strain The following Table 3 shows the maximum, minimum and average values of the enzymatic activities and reduction ratios (parent 100%) of Phase III mutant strains shown in Table 2 except S. mutans Attenuated Strain K-III.

TABLE 3

| Phase III strain | Sucrase | GT-ase | Invertase |
|---|---|---|---|
| Activity max. | 57.6 | 41.4 | 37.6 |
| min. | 23.7 | 13.3 | 8.0 |
| average | 46.1 | 25.6 | 23.45 |
| Reduction % max. | 12.8 | 17.6 | 18.29 |
| min. | 2.57* | 3.50* | 1.94* |
| average | 9.98 | 11.96 | 10.11 |

*Phase III strain induced from NCTC 10449.

The following Tables 4-6 correspond respectively to Tables 1-3 and indicate the corresponding figures of Phase III-like wild type strains.

TABLE 4

(Phase III like strains)

| Strain (TMD-NC) | Ag | Ma | So | Ra | Sa | Ce | Me | La | Su | Es |
|---|---|---|---|---|---|---|---|---|---|---|
| Inoue | 256 | + | + | + | + | + | + | + | + | + |
| T. Komatsu | 2048 | + | + | + | + | + | + | + | + | + |
| K. Komatsu | 1024 | + | + | + | − | + | + | + | + | + |
| Kawabe | 1024 | + | + | + | + | + | + | + | + | − |
| Nakayama | 1024 | + | + | + | − | + | + | + | + | − |
| Kume* | 1024 | + | + | + | − | + | − | + | + | + |
| 26P | 256 | + | + | + | + | + | + | + | + | + |
| 49 | 256 | + | + | + | + | + | + | + | + | + |
| 57-4 | 1024 | + | + | + | + | + | + | + | + | + |
| NCTC10449** | 2048 | + | + | − | − | + | + | + | + | + |

*All strains are Human I type (serotype c) except Kume (Human II type; serotype d).
**Reference (Phase I strain).
Other decompositions are the same as those of S. mutans NCTC 10449 (serotype c).
Ag: agglutination titre, Ma: mannitol, So: sorbitol, Ra: raffinose, So: sorbitol, Sa: salicin, Ce: cellobiose, Me: mellibiose, La: lactose, Su: sucrose, Es: esculin Table 4 indicates examples of Phase III-like strains which we have isolated from the oral cavity of more than 1000 humans.

TABLE 5

Enzymatic activities of Phase III-like strain.

| Strain (TMD-NC) | Sucrase | GT-ase | Invertase |
|---|---|---|---|
| Inoue | 0.57 | 0.28 | 0.28 |
| | 10.69 | 9.30 | 12.07% |
| K. Komatsu | 0.44 | 0.16 | 0.28 |
| | 8.26 | 5.32 | 12.07% |
| T. Komatsu | 0.39 | 0.15 | 0.28 |
| | 7.32 | 4.98 | 9.91% |
| Kawabe | 0.56 | 0.25 | 0.31 |
| | 10.51 | 8.31 | 13.36% |
| Nakayama | 0.46 | 0.25 | 0.20 |
| | 8.63 | 8.31 | 8.62% |
| Kume (*1) | 0.35 | 0.14 | 0.24 |
| | 6.57 | 4.65 | 10.34% |
| 26P (*2) | 0.43 | 0.17 | 0.28 |
| | 8.07 | 5.65 | 12.07% |
| 49 (*3) | 0.37 | 0.17 | 0.20 |
| | 6.94 | 5.65 | 8.62% |
| 57-4 (*4) | 1.30 | 0.29 | 1.00 |
| | 24.40 | 9.63 | 43.10% |
| NCTC10449 (*5) | 5.33 | 3.01 | 2.32 |
| | 100.00 | 100.00 | 100.00% |

Note:-
*1...FERM BP-319, NRRL B-15433; *2...FERM P-6876, NRRL B-15430;
*3...FERM BP-318, NRRL B-1543; *4...FERM P-6878, NRRL B-15432; *5...reference strain, Phase I.

TABLE 6

| Phase III-like strains | | Sucrase | GT-ase | Invertase |
|---|---|---|---|---|
| Activity | max. | 1.30 | 0.29 | 1.00 |
| | min. | 0.35 | 0.14 | 0.20 |
| | average | 0.54 | 0.21 | 0.34 |
| Reduction* (%) | max. | 24.40 | 9.63 | 43.10 |
| | min. | 6.57 | 4.65 | 8.62 |
| | average | 10.15 | 6.85 | 14.46 |

(Note:-*NCTC10449 = 100%)

The numerical values of NCTC 19449 shown in Table 2 are inconsistent with the numerical values of NCTC 10449 shown in Table 5 since the measurements were not effected at the same time.

Table 4 indicates the characteristics (agglutination titres and decompositions of sugars) of certain Phase III-like strains isolated from the oral cavity of humans.

By comparing Tables 1-3 with Tables 4-6, the following obervations may be given:

(1) the charcateristics of naturally-occuring Phase III-like strains are closely similar to the characteristics of Phase III mutant strains;

(2) it appears that glucosyltransferase is the enzyme which directly participates in the induction of dental caries by S. mutans.

(3) With respect to the enzymatic activities and agglutination titres, there is a difference between the inhibiting abilities of respective strains.

(4) The decomposition spectra of sugars of Phase III like (and Phase III) strains are are broader than the corresponding spectra of Phase I strains, for example, NCTC10449.

Further expriments have revealed that Phase III-like strains are superior to Phase III mutant strains with respect, for example, to the fact that Phase III-like strains do not produce a detectable amount of acetic acid. Moreover, it is believed, in general, that the genetical stability of naturally-occuring strains is superior to that of mutant strains induced from wild type strains by mutagensis.

Phase III-like strains of S. mutans of the present invention may be obtained, for example, in the following manner:

In one embodiment, dental plaque was collected from the oral flora of humans and cultured anaerobically at 37° C. for 24–48 hours. The colonies similar to the colonies of Phase III mutant strains as herenbefore described were selected and further cultured. The grown strains were further selected with reference to, for example, the reduced ability to form plaque in vitro and the reduced cariogenicity in vivo, for example by using hamsters. The selected strains were finally administered to animals which were then pathogenically examined, with reference to "A. Test Methods for General Test Standard for Biological Medicines" issued by The Ministry of Welfare, Japanese Government (1979). No unusual thing was noted.

Phase III-like strains of the present invention may be cultured in conventional manner used for culturing various streptococci, preferably under anaerobic conditions at 10°–39° C. (for example about 37° C.) and at a pH of 5–8 (e.g. about 7) for 24–72 hours. For mass propagation, the use of liquid media may be preferred. After completion of culturing, the living cells in the cultured broth amount usually to more than $10^{10}$ cells/ml.

Any and all carriers or excipients suitble for oral administration may be used for the purpose of the present invention. Thus, it is possible, if desired, to admininister the cultured liquor without any after-treatment to the human oral cavity. However, it is preferred to add the cultured liquor to an appropriate liquid carrier known per se in the preparation of various liquid foodstuffs e.g. drinks containing the living cells of edible lactic acid-producing bacilli. Also it is preferred to separate the cells from the cultured broth in conventional manner (e.g. by centrifugation, 8000 r.p.m./min.) and suspend the same in an appropriate liquid carrier such as, for example, water, syrup, animal milk etc. It is also possible to freeze-dry the separated cells in conventional manner and divide into appropriate dosage unit forms for preservation, if desired, in association with a suitable preservative such as, for example, milk sugar, gelatin and the like. In this manner, it is possible to preserve the viable cells over an extended period of time. For use, the viable cells may preferably be dispersed in a suitable liquid carrier although it is possible to administer directly and orally the cultured broth to humans.

As they are incapable of forming plaque theselves and moreover their ability to adhere is essentially weak, it is preferred to use a large amount of the non-cariogenic composition of this invention. Usually, for example, 50–100 ml of a liquid composition containing about $10^5$–$10^7$ viable cells/ml or 50–100 g of a solid or semi-solid composition containing a same number of the viable cells per gram may be administered everyday once after meals. In this manner, the cariogenic strains of *S. mutans* may substantially be reduced or disappear from the oral cavity, for example, in one or two weeks after the beginning of administration. If desired, a higher concentration (e.g. more than $10^8$ viable cells/ml or g) may be used.

It may be indeed possible to admix the living cells of the non-cariogenic strain of this invention with foodstuffs containing the living cells of lactic acid-producing bacilli such as e.g. cheese, pickles and the like, if desired. However, it is especially advantageous to mix the non-cariogenic strain of this invention with a drink known per se containing the living cells of edible lactic acid-producing bacilli whereby to prevent or inhibit dental caries easily and comfortably. Various animal test have revealed moreover that the induction of dental caries by the known edible lactic acid-producing bacilli may completely be prevented or inhibited by using such a mixture without any observable side effect.

Lactic acid-producing bacilli denote the bacilli which produce lactic acid from sugars and are classified into Gram-positive bacilli such as streptococci and Gram-negative bacilli such as lactobacilli. Various liquid and solid foodstuffs containing the living cells of such bacilli have been used over many years in various countries of the world owing to a belief that they are biologically active against the growth of harmful microorganisms in the intestinal flora of humans. However, it is well known that such bacilli have a cariogenic potential, and, for example, *Lactobacillus acidophilus, L. casei, L. helvetius* and *Streptococcus faecalis* are well known as aetiological factors. Moreover, we have recently found that certain strains of the genus Bifidobacterium such as, for example, *B. longum, B. bifidum. B. bruve* and the like, which are nowadays admired in Japan and other countries for the preparation of yogurts and the like produce a very large amount of acetic acid. We have confirmed by animals tests that, when such strains of Bifidobacterium intrude into dental caries already formed, for example, by the action of cariogenic *S. mutans* and reside there, the acetic acid produced by them can give rise to a heavy damage to the teeth structure. Animal test have revealed that the non-cariogenic strains of *S. mutans* of this invention are sucessfully competitive with various cariogenic oral baccili.

According to an ordinance issued by the Ministry of Welfare of the Japanese Government, which is entitled Specifications of Milks and Milk Products under the Food Sanitation Law of Japan, the edible lactic acid-producing bacilli denoted by law are such bacilli capable of forming yellowish colonies by culturing a sample on a bromocresol purple-containing plate counter medium at 35°–37° C. for 72 hours. As Phase III-like strains of this invention fall completely within this requirement, it is possible to use the non-cariogenic strains of this invention for edible purpose solely or in combination with other edible lactic acid-producing bacilli.

The preparation of yogurt is well known in the art and comprises, in general, sterilizing milk, adding to the the sterilized milk a starter (seed culture) and culturing the same at a suitable temperature to obtain a solid curd. More specifically, yogurt may be produced, for example, by concentrating a milk, adding, if desired, to the solution sucrose (8–9%), agar etc. to give an adjusted solid content (12–14%), sterilizing the mixture at 85°–90° C. for 30 minutes cooling the mixed solution to 33°–40° C., adding a starter to the solution, putting the mixture into a yogurt bottle, culturing the starter at a suitable temperature (e.g. 33°–37° C.) for a suitable time (e.g. 10–15 hours) to give an acidity of 0.8–1.2, discontinuing the fermentation and preserving the bottle at a cool temperature. In another embodiment, yogurt may be prepared by adding a suitable amount of 5% glucose or sucrose solution to a skim milk to give 10% solids, adding a starter (2–2.5%) to the mixture, culturing the starter at a suitable temperature for a suitable time (e.g. 24–72 hours) to give an acidity of 0.8–1.2%, discontinuing the fermentation, homogenizing the culture broth with agitation, and adding a 10% sucrose solution to the fermented liquor. Suitable sweatening agents, essences, preservatives etc. may be added to the product. It is also known to replace at least a part of the animal milk by soybean milk. In general, yogurts commercially available in Japan contain, for example, milky solids (12-14%), sucrose (6-8%), lactic acid (1%) and the living cells of lactic acid-producing bacilli (at least $10^8$ cells/ml).

Where the non-cariogenic strains of this invention are added to yogurt and the like having similar contents, it is sufficient to add the non-cariogenic strain of this invention at a concentration of about $10^5$-$10^7$ cells/ml. In such a case, it is possible to completely prevent or inhibit dental caries induced by cariogenic strains of S. mutans and lactic acid-producing bacilli without significant side effect upon the quality of the drink per se. Although it is possible, if desired, to use a large amount of the living cells of the non-cariogenic strain of this invention, but the use of an excessively small amount of the living cells should be avoided since the adhering ability of Phase III-like strains is relatively low.

For example, where a drink containing about $10^7$-$10^9$, e.g. $10^8$ cells/ml of conventional lactic acid-producing bacilli and about $10^6$ living cells/ml of the non-cariogenic strain of this invention was administered to humans at a dose of 50-100 ml once daily after meals, the concentration of the cariogenic strains of S. mutans decreased continuously and finally disappeared from the oral cavity about 1-2 weeks after the beginning of the administration. Various experiments using humans and hamsters have revealed that dental caries induced by S. mutans and other lactic acid-producing bacilli may be completely prevented or inhibited by using the non-cariogenic compositionh of this invention, for example, in the form of a mixed drink.

After being preserved for 10 days at a low temperature (e.g. not higher than 10° C.), the number of living cells of the non-cariogenic strain of this invention and lactic acid-producing bacilli in the mixed drink as well as other properties of the drink were substantially unchanged. The mixed cells of this invention do not exert any adverse influence upon the flavour and taste inherent in the drink containing lactic acid-producing bacilli. Thus, the mixed drink of this ivention exhibits synergistic effects obtained by the combined use of the non-cariogenic strains of the present invention and conventional lactic acid-producing bacilli.

Freeze-dried composition may be preserved over an extended period of time. Such a composition may be prepared by freeze-drying the cultured broth of Phase III-like strains in conventional manner. It is also possible to mix-culture Phase III-like strains with suitable bacilli capable of producing edible lactic acid. If desired, the living cells of Phase III-like strains from the cultured broth, followed by freeze-drying. The freeze-dried viabl cells may be preserved over an extended period of time preferbly at low temperature.

The solid or semi-solid composition may contain e.g. about 10 −10 viable cells per gram of the composition.

Various carriers and/or excipients suitbale for oral administration which are well known in the art may be used for the purpose of this invention. The non-cariogenic composition may, if desired, further contain various known additives such as, for example, preservatives, hardening agents, lubricants, emulifiers, stabilizers, essence and the like.

With respect to the inhibiting activity, no significan difference is observed between Phase III-like strains of Human I and II types, presumably because they are deficient in the plaque-forming ability and intrude compulsively into the plaque or support medium of other bacilli to reside there so that other bacilli are destroyed outwardly and die. The plaque occupied by the invaders is destructed into pieces and Phase III-like strains also die.

The following non-limiting examples and experiments illustrate the invention, wherein culturing was effected at 37 C in a nitrogen atmosphere (90%) containing $CO_2$ gas (5%) and hydrogen gas (5%) unless otherwise specified.

EXAMPLE 1

A 5% glucose solution containing skim milk (10% as solids) was sterilized at 110° C. for 15 minutes. To this solution *Lactobacillus casei* was inoculated and cultured for 36 hours in conventional manner. The cultured liquor was homogenized with agitation to obtain a first solution. Separately, *Streptococcus mutans* TMD-NC 49 (FERM BP 318; NRRL B-15431) was cultured in a similar manner to that described above and the cultured liquor was homogenized to obtain a second solution. To a 10% fructose solution, the thus-obtained first and second solutions were added to obtain a mixed drink of this invention containing about $10^8$ living cells/ml of *L. casei* and about $10^6$ living cells/ml of *S. mutans* TMD-NC 49. Separately, the first solution was added to a 10% fructose solution to obtain a control drink containing about $10^8$ living cells/ml of *L. casei*. The flavour and taste of the mixed drink were superior to those of the control drink.

EXAMPLE 2

*Streptococcus mutans* TMD-NC 49 (FERM BP 318; NRRL B-15431) was cultured for 36 hours on Todd Hewitt Broth (BBL., U.S.A.; pH=7.2). The living cells were separated from the cultured broth by centrifugation (8000 r.p.m./20 min.). The cells and the first solution obtained by the method of Example 1 were added to a 10% fructose solution to obtain a mixed solution containing about $10^8$ cells/ml and about $10^6$ cells/ml of *L. casei* and *S. mutans* TMD-NC 49 respectively. Similarly, a control drink containing about $10^8$ cells/ml of *L. casei* alone was prepared. In comparison with the control drink, the mixed drink exhibited better flavour and taste.

EXAMPLE 3

In a similar manner to that described in Example 1, *Streptococcus mutans* TMD-NC Kume (FERM BP 319;NRRL B-15433) was used to prepare a mixed drink containing *S. mutans* TMD-NC 49 and *S. mutans* TMD-NC Kume (about $10^6$ cells/ml respectively).

EXAMPLE 4

Preparation of freez-dried composition

*S. mutans* TMD-NC 49 was cultured in a similar manner to that described in Example 2. The cells were collected from the culture broth by centrifugation (8000 r.p.m./20 min.) and suspended in skim milk solution (10% solids containing 0.2% of glucose). The cell suspension was freeze-dried in conventional manner. The concentration of the cells was adjested to about $10^8$ cells/g of the product.

EXPERIMENTS

In the following experiments, the following materials were used, to which various additives such as, for example, essences, hardening agents, preservatives and the like were conveniently not added.

(1) Material I corresponds to the control drink used in Example 1 and contains the living cells of *Lactobacillus casei* (about $10^8$ cells/ml). Material II corresponds to the mixed drink of Example 2 and contains the living cells of *L.casei* (about $10^8$ cells/ml) and *S. mutans* TMD-NC 49 (FERM BP-317; about $10^6$ cells/ml). Material III was prepared by culturing *S. mutans* NCTC 10449, a typical cariogenic wild strain by the method of Example 2, separating the cells from the culture broth and adding the cells to Material I to obtain a cariogenic drink containing about $10^8$ living cells of *S. mutans* NCTC 10449 and about $10^8$ living cells of *L. casei* per ml.

(2) As test animals, Golden hamsters (each group consisting of 10 hamsters otherwise specified) were used and bred on a cariogenic diet (Diet 2000, Funabashi Nojo, Japan) ad libitum.

(3) In the experiments hereinafter described, the lactic acid-producing microorganism used was *L. casei* unless otherwise specified.

Although various tests were effected by using *Lactobacillus acidophilus, L. bulgaricus, L. bifidus, Streptococcus thermophilus* and *S. lactis*, no significant differnce was observed in so far as the prevention and inhibition of dental caries induction was concerned. As described hereinbefore, certain strains of the genus *Bifidobacterium* which are nowadays admired in Japan and various other countries of the world are characterized by their higher productivity of lactic acid and acetic acid, when compared, for example, with *L. casei* which does not produce a detectable amount of acetic acid. The acetic acid can give rise to heavy damage to the structure of teeth. It has been confirmed that the present nongenic compositions are capable of succcessfully competing with the strains of Bifidobacterium.

EXPERIMENT 1

Materials I (*Lactobacillus casei*) and II (*L. casei* and *S. mutans* TMD-NC 49 (FERM BP-318) were administered to hamsters to find out that the cariogenic potential of *S. mutans* TMD-NC 49 was negative. The test period was 60 days. From 21 days after birth (weaning period), Material I (0.1 ml once daily) was administered into the buccal cavity of Group I, and similarly Material II was administered to Group II. Samples were optionally collected from the molar surfaces of Group II, and each sample was cultured for 48 hours on a TYC agar plate medium (15 ml;pH 7.2) and a Mitis-salivarius agar plate medium (15 ml;pH 7.2; containing 100 μg of bacitracin) to investigate the adherence of TMD-NC 49 to the teeth. Although its adhering ability was lower than that *S. mutans* NCTC 10449, a typical cariogenic wild strain, TMD-NC 49 adhered to the teeth about 6–12 days after the beginning of administration. After completion of breeding, all animals were anesthetised with pentabarbital and abdominally injected with pilocarpin, HCl (0.75%; each 0.1 ml/100 g of body weight). The saliva was collected from each animal which was then killed by cardic puncture. The maxilla was removed from the animal and treated in an autoclave at 120° C. for 1–2 minutes to remove the soft part. The remaining part was washed with water to obtain a sample of the teeth. The results shown in Table 7 were calculated from the numbers of all molars and infected molars of each group, from which it is apparent that the cariogenic potential of *S. mutans* TMD-NC 49 was negative.

TABLE 7

|  | A | B | C |
|---|---|---|---|
| Group I | 78.3 | 10.0 | 0.93 |
| Group II | 75.2 | 0. | 0. |

Group I: *L. casei*
Group II: *L. casei* and *S. mutans* TMD-NC 49
A: Increased body weight (% in average)
B: Infection rate (all hamsters = 100%)
C: Infection rate (all molars = 100%)

Material II (*Lactobacillus casei* and *S. mutans* TMD-NC 49 (0.2 ml/day) was continuously administered to hamsters for 3 months. The hamsters were then killed and examined pathogenically, but nothing unusual was observed.

EXPERIMENT 2

Materials II (*Lactobacillus casei* and *S. mutans* TMD-NC 49; FERM BP 318) and III (*S. mutans* NTCC 10449 and *L. casei*) were administered to hamsters to investigate the inhibiting activity of *S. mutans* TMD-NC 49 on the induction of dental caries. The test period was 60 days. Between the 10th and 27th days after birth (teething period of molars), on every other days Materials II and III were in turns administered into the buccal cavities of Group I (test group) at a daily dose of 0.1 ml once. From 21 days after birth, the animals were bred with a cariogenic diet (Diet 2000) alone. Group II was treated in a similar manner to that applied to Group I except that Material II was not used. The third group was bred with Diet 2000 without administering Materials II and III.

After completion of breeding, all molars were investigated in a similar manner to that described in Experiment 1 to obtain the results shown in Table 8, from which the activity of *S. mutans* TMD-NC 49 against cariogenic potential is apparent.

TABLE 8

|  | I | II | III |
|---|---|---|---|
| A. | 71.7 | 68.3 | 70.4 |
| B. | 20. | 100. | 0. |
| C. | 5.* | 56.7** | 0. |

(Notes:-*6/120; **68/120)
Group I: *L. casei* and *S. mutans* TMD-NC 49 (FERM BP318)
Group II: *L. casei* and *S. mutans* NTCC 10449
Group III: Untreated
A: Increased body weight (% in average)
B: Infection rate (all hamsters = 100%)
C: Infection rate (all molars = 100%)

EXPERIMENT 3

Material II (*L. casei* and *S. mutans* TMD-NC 49; FERM BP 318;) was administered to seven members of a family consisiting of 8 members including an infant of 4 years old (host of *S. mutans* TMD-NC 49). Before this, samples were collected from their oral floras. Each sample was suspended in a physiological solution of sodium chloride (pH 7.0; 0.2 ml) and treated with ultrasonic waves (20 KHz/5–10 min.) to give a precipitate which was then cultured for 24 hours on a Mitissalivarius agar plate medium (15 ml; pH 7.2; containing 100 μg of bacitracin) confirm that the cariogenic wild strains of *S. mutans* ('c' to 'g' serotypes) were living in their oral floras, confirmation being effected by comparison of the biochemical and serological characteristics of the microorganisms.

Material II (each 50 ml/once daily) was then administered into the buccal cavities of the members of the family every day 3 hours after breakfast. During the test period, no special treatment was paid to the members of the family in order to prevent the induction of dental caries except for the use of a commercial tooth paste (White & White; Lion K.K., Tokyo; containing anhydrous silicic acid, wetting agent, bonding agent etc.) twice daily after breakfast and dinner. Optionally, samples were collected from their oral floras and treated in a similar manner to that described above to investigate the disappearance of the cariogenic wild strains of *S. mutans* and the adherence of *S. mutans* TMD-NC 49 onto the teeth. It was found that the cariogenic wild strains disappeared from the oral floras of 2 members of the family 9 days after the begining of the administration of TMD-NC 49, and from the other members of the family about 2 weeks after the beginning. After disappearance of the cariogenic strains, the administration was continued to all members of the family for 6 months with an interval of 3 days, and further continued to 3 members of the family for an additional 6 months. When the administration was discontinued, *S. mutans* TMD-NC 49 disappeared from the oral floras in a relatively short period of time, but no cariogenic strain of *S. mutans* was detected in any of the family during the administration of TMD-NC 49.

EXPERIMENT 4

A similar experiment to that described in Experiment 1 was carried out with the exception that *Bifidobacterium longum* (for Materials IA, IIA and IIIA), *B. bruve* (for Materials IB, IIB and IIIB) and *B. bifidum* (for Materials IC, IIC and IIIC), which are capable of producing larger amounts of lactic acid and acetic acid, instead of L. casei which does not produce a detectable amount of acetic acid. Groups 1–3 were the test animals and Groups 4–6 were the control groups The animals of Group 7 were bred on a cariogenic diet (Diet 2000) without administration of the lactic acid-producing strains and non-cariogenic *S. mutans* TMD-NC 49. The test period was 40 days. From 21 days after birth, animals of Groups 1, 2 and 3 were administered respectively with Materials IIIA, IIIB and IIIC. A dose of 0.2 ml was administered into the buccal cavity of each animal once daily. During the test period, all animals were bred on Diet 2000 ad libitum. After the test period, all animals were treated in a similar manner to that described in Experiment 1 to obtain the results shown in the following Table 9, from which the effect of the present non-cariogenic composition is apparent. The concentration of the living cells of *S. mutans* TMD-NC was about $10^6$/ml, and the concentration of the living cells of Bifidobacterium was about $10^8$/ml. The strains of Bifidobacterium were collected from yogurts sold in commenon market in Japan and subcultured.

TABLE 9

| | 1 | 2 | 3 | 4 | 5 | 6 | 7 |
|---|---|---|---|---|---|---|---|
| A | 61.6 | 61.4 | 61.8 | 62.8 | 60.1 | 61.7 | 68.2 |
| B | 40 | 30 | 10 | 100 | 80 | 100 | 0% |
| C | 7/120 | 4/120 | 2/120 | 19/108 | 29/108 | 31/108 | 0% |

TABLE 9-continued

| 1 | 2 | 3 | 4 | 5 | 6 | 7 |
|---|---|---|---|---|---|---|
| 5.8 | 3.3 | 1.7 | 17.6 | 24.2 | 25.8 | 0% |

Group 1: *B. longum* and *S. mutans* TMD-NC 49
2: *B. bruve* and *S. mutans* TMD-NC 49
3: *B. bifidum* and *S. mutans* TMD-NC 49
4: *B. longum*
5: *B. bruve*
6: *B. bifidum*
7: Untreated
A: Increased body weight (% in average)
B: Infection rate (all hamsters = 100%)
C: Infection rate (all molars = 100%)

Similar results were obtained by the use of a freeze-dried composition containing about 10 viable cells of *S. mutans* TMD-NC 49 per gram.

REFERENCE

Preparation of *Streptococcus mutans* Attenuated Strain K-III (FERM BP 316;NRRL B-15529)

Wild type strains of *S. mutans* collected from the dental plaque of a human (adult) were cultured in a similar manner to that described in the following Experiment 1, and "c" type strains were identified by referring to their known biological and serological characteristics. These wild type strains were cultured at 37° C. for 24 hours on a Todd Hewitt Broth (20 ml; pH 7.8; BBL, U.S.A.). The cultured broth was centrifuged (8000 r.p.m./20 min.) at 4° C. to separate the cells which were washed 3 times by centrifugation (8000 r.p.m./20 min, each) at 4° C. using a 1/75M phosphate buffered solution of sodium chloride solution (each 100 ml; pH=6.8), followed by suspending the cells in a 1/75M phosphate buffered sodium chloride solution (pH 6.8; containing 0.1% of nitrogen mustard) at a concentration of about $10^6$ cells/ml. The suspension was kept at 37° C. until more than 90% of the cells were killed. The suspension was centrifuged (8000 r.p.m./20 min.) to separate the cells which were then cultured in a similar manner to that used above on a Todd Hewitt Broth (20 ml). The cultured broth (one platinum loopful) was cultured anaerobically on a TYC agar plate medium (pH about 7.2; 15 ml) at 37° C. for 48 hours. The cultured broth was allowed to stand at ambient temperature for 24 hours. Colonies having a weaker productivity of insoluble and water-soluble DPS were selected and combined. The above-mentioned soluble DPS were selected and combined. The above-mentioned procedure was, if desired, repeated until the desired strain was obtained. Colonies of the desired strain were easily located as the DPS were formed, for example, on the surface of the colonies grown on the surface of TYC agar plate medium. The colonies with a reduced production of DPS were medium. The colonies with a reduced production of DPS were separated and subcultured by using a suitable liquid media. It was also possible to determine the productivity of DPS, for example, by an appropriate enzymatic method known per se. No significant ingravescence of the characteristics of the strain was noted and generation of other cariogenic strains was not found on subculturing the present mutant strain e.g. on TYC agar media or on treatment with various known mutagents. By administration of the resultant mutant strain to humans or hamsters for a long period of time, it was found that the resultant mutant strain possessed a reduced cariogenic potential.

We claim:

1. A composition for inhibiting human dental caries, which comprises as active ingredient, an effective amount of the viable cells of at least one strain of a purely-cultured, naturally-occuring microorganism in association with a carrier or excipient suitable for oral administration, said strain having the following characteristics, namely being:
   (a) isolated as a naturally-occurring microorganism from the oral cavity of humans and purely cultured;
   (b) capable of inhibiting the growth of cariogenic strains of *Streptococcus mutans* and edible lactic acid-producing in bacilli in vivo and in vitro;
   (c) substantially deficient in the productivity of water-soluble and insoluble dextran-like polysaccharides and gluosyltransferase activity;
   (d) substantially deficient in cariogenic potential in the oral cavity of humans; and
   (e) classified as a strain of *Streptococcus mutans*.

2. The composition of claim 1 in a form selected from the group consisting of liquid, semi-solid and solid compositions.

3. The composition of claim 2, wherein the concentration of the viable cells is from about $10^5$ to $10^7$ cells per ml of the composition.

4. The composition of claim 2 in the form of a freeze-dried composition.

5. The composition of claim 2 in the form of a foodstuff.

6. The composition of claim 5, wherein the carrier comprises a mammal's milk.

7. The composition of claim 6 in the form of a drink containing viable cells of edible lactic acid-producing bacilli.

8. The composition of claim 7, wherein the concentration of the viable cells of edible lactic acid-producing bacilli is from about $10^7$ to $10^9$ cells per ml of the composition.

9. A composition for inhibiting human dental caries, which comprises as active ingredient an effective amount of the viable cells of at least one strain of a purely-cultured microorganism, in association with a carrier or excipient suitable for oral administration, said strain of having the following characteristics, namely being:
   (a) isolated as naturally-occurring microorganism from the oral cavity of humans and purely cultured;
   (b) capable of inhibiting the growth of cariogenic strains of *Streptococcus mutans* and edible lactic acid-producing bacilli in vivo and in vitro;
   (c) substantially deficient in the productivity of water-soluble and insoluble dextran-like polysaccharides and glucosyltransferase activity;
   (d) substantially deficient in cariogenic potential in the oral cavity of humans and hamsters; and
   (e) classified as a strain of *Streptococcus mutans*;
   wherein said strain of microorganism is selected from the group consisting of *Streptococcus mutans* TMD-NC Kume (FERM BP-319), *Streptococcus mutans* TMD-NC 26P (FERM BP-6876), *Streptococcus mutans* TMD-NC 49 (FERM BP-318), *Streptococcus mutans* TMD-NC 57-4 (FERM BP-3064), *Streptococcus mutans* TMD-NC Inoue (FERM-BP 3058), *Streptococcus mutans* TMD-NC T. Komatsu (FERM-BP 3059), *Streptococcus mutans* TMD-NC K. Komatsu (FERM-BP 3060), *Streptococcus mutans* TMD-NC Kawabe (FERM-BP 3061), and *Streptococcus mutans* TMD-NC Nakayama (FERM-BP 3062) and mutations thereof.

10. The process of claim 9, wherein the strain isolated is selected from the group consisting of *Streptococcus mutans* TMD-NC Kume (FERM BP-319), *Streptococcus mutans* TMD-NC 26P (FERM BP-6876), *Streptococcus mutans* TMD-NC 49 (FERM BP-318), *Streptococcus mutans* TMD-NC 57-4 (FERM BP-3064), *Streptococcus mutans* TMD-NC Inoue (FERM-BP 3058), *Streptococcus mutans* TMD-NC T. Komatsu (FERM-BP 3059), *Streptococcus mutans* TMD-NC K. Komatsu (FERM-BP 3060), *Streptococcus mutans* TMD-NC Kawabe (FERM-BP 3061), and *Streptococcus mutans* TMD-NC Nakayama (FERM-BP 3062).

11. A process for the preparation of an oral composition for preventing or inhibiting dental caries induced by *Streptococcus mutans* and edible lactic acid-producing bacilli, comprising the steps of isolating a microorganism from the oral cavity of a human, purely culturing the same and mixing an effective amount of the purely cultured living cells with a carrier or excipient suitable for oral administration, wherein said strain is
   (a) capable of inhibiting the growth of cariogenic strains of *Streptococcus mutans* and edible lactic acid-producing bacilli in vivo and in vitro;
   (b) substantially deficient in the productivity of water-soluble and insoluble dextran-like polysaccharides and glucosyltransferase activity;
   (c) substantially deficient in cariogenic potential in the oral cavity of humans and hamsters; and
   (d) classified as a strain if *Streptococcus mutans*.

* * * * *